United States Patent [19]
Meyer, Jr. et al.

[11] Patent Number: 6,136,601
[45] Date of Patent: *Oct. 24, 2000

[54] TARGETED MUTAGENESIS IN LIVING CELLS USING MODIFIED OLIGONUCLEOTIDES

[75] Inventors: Rich B. Meyer, Jr., Bothell; Howard B. Gamper, Woodinville; Igor V. Kutyavin; Alexander A. Gall, both of Bothell, all of Wash.

[73] Assignee: Epoch Pharmaceuticals, Inc., Redmond, Wash.

[ * ] Notice: This patent issued on a continued prosecution application filed under 37 CFR 1.53(d), and is subject to the twenty year patent term provisions of 35 U.S.C. 154(a)(2).

[21] Appl. No.: 08/827,117

[22] Filed: Mar. 26, 1997

Related U.S. Application Data

[63] Continuation-in-part of application No. 08/485,611, Jun. 7, 1995, Pat. No. 5,849,482, which is a continuation-in-part of application No. 08/178,733, Jan. 7, 1994, abandoned, which is a continuation of application No. 07/748,138, Aug. 21, 1991, abandoned.

[51] Int. Cl.[7] .............................. C12Q 1/68; C07H 21/04
[52] U.S. Cl. .............................. 435/375; 435/6; 536/24.3; 536/24.31; 536/24.33; 536/24.5
[58] Field of Search .......................... 435/6, 315; 514/44; 536/24.5, 24.3, 24.31, 24.33

[56] References Cited

U.S. PATENT DOCUMENTS

| | | | |
|---|---|---|---|
| 3,598,807 | 8/1971 | Nakayama et al. | 475/5 |
| 3,962,211 | 6/1976 | Townsend et al. | 435/6 |
| 4,123,610 | 10/1978 | Summerton et al. | 536/25.3 |
| 4,582,789 | 4/1986 | Sheldon, III et al. | 435/6 |
| 4,599,303 | 7/1986 | Yabusaki et al. | 435/6 |
| 4,711,955 | 12/1987 | Ward et al. | 536/25.32 |
| 4,766,062 | 8/1988 | Diamond et al. | 435/6 |
| 4,795,700 | 1/1989 | Dervan et al. | 435/5 |
| 4,835,263 | 5/1989 | Nguyen et al. | 536/24.3 |
| 4,837,311 | 6/1989 | Tam et al. | 536/27.14 |
| 4,849,513 | 7/1989 | Smith et al. | 536/26.6 |
| 4,888,274 | 12/1989 | Radding et al. | 435/6 |
| 4,910,300 | 3/1990 | Urdea et al. | 536/26.8 |
| 4,948,882 | 8/1990 | Ruth | 536/25.32 |
| 5,015,733 | 5/1991 | Smith et al. | 536/27.23 |
| 5,176,996 | 1/1993 | Hogan et al. | 435/6 |
| 5,422,251 | 6/1995 | Fresco | 435/91.1 |
| 5,541,313 | 7/1996 | Ruth | 536/24.3 |
| 5,574,142 | 11/1996 | Meyer, Jr. et al. | 536/23.1 |
| 5,776,744 | 7/1998 | Glazer et al. | 435/463 |

FOREIGN PATENT DOCUMENTS

| | | |
|---|---|---|
| 021293 | 1/1981 | European Pat. Off. . |
| 214908 | 9/1986 | European Pat. Off. . |
| 198207 | 10/1986 | European Pat. Off. . |
| 227459 | 7/1987 | European Pat. Off. . |
| 242264 | 10/1987 | European Pat. Off. . |
| 259186 | 3/1988 | European Pat. Off. . |
| 266099 | 5/1988 | European Pat. Off. . |
| 267996 | 5/1988 | European Pat. Off. . |
| 375406 | 12/1989 | European Pat. Off. . |
| 375408 | 6/1990 | European Pat. Off. . |
| 3310337 | 9/1984 | Germany . |
| 61-109797 | 5/1986 | Japan . |
| WO 84/03285 | 8/1984 | WIPO . |
| WO 85/02628 | 6/1985 | WIPO . |
| WO 85/03075 | 7/1985 | WIPO . |
| WO 86/02929 | 5/1986 | WIPO . |
| WO 86/04816 | 8/1986 | WIPO . |
| WO96/41008 | 12/1986 | WIPO . |
| WO 87/07611 | 12/1987 | WIPO . |
| WO 88/10264 | 12/1988 | WIPO . |
| WO 90/03370 | 4/1990 | WIPO . |
| WO 90/14353 | 11/1990 | WIPO . |
| WO 90/15884 | 12/1990 | WIPO . |
| WO 91/18997 | 12/1991 | WIPO . |
| WO 92/20698 | 11/1992 | WIPO . |
| WO 93/03736 | 3/1993 | WIPO . |
| WO 94/17092 | 8/1994 | WIPO . |
| WO 95/01364 | 1/1995 | WIPO . |
| WO 96/40711 | 12/1996 | WIPO . |
| WO96/39195 | 12/1996 | WIPO . |
| WO96/40271 | 12/1996 | WIPO . |
| WO96/40898 | 12/1996 | WIPO . |

OTHER PUBLICATIONS

M. Cooney et al. Scienie 241:456–9 '88.
L. Pauling C&E News 24(10) 1375–6 '46.
R. Dickenson et al, The Struct. & Action of Proteins, Benjamin/Cummings Publ. Co., Menlo Park, CA '69, p. 68.
J. Goodchild Bioconj. Chem. 1(3) 166–87 '90.
Dialog Abstract to EP 214,908, provided as Derwent World Patent Index Acc No. 87–074186/198711.
Averbeck, D., "Relationship between lesions photoinduced by mono– and bi–functional furocoumarins in DNA and genotoxic effects in diploid yeast" *Mutation Res.* 151:217–233 (1985).
Giovannangéli et al., "Oligodeoxynucleotide–directed photo–induced cross–linking of HIV proviral DNA via triple–helix formation" *Nucleic Acids Res.* 20(16):4275–4281 (1992).

(List continued on next page.)

*Primary Examiner*—John L. LeGuyander
*Attorney, Agent, or Firm*—Morrison & Foerster, LLP

[57] ABSTRACT

A method for introducing a site-specific mutation into a target polynucleotide sequence is presented. The method involves the use of an oligonucleotide capable of binding to the target sequence, either by triplex formation (mediated by Hoogsteen, reverse Hoogsteen or equivalent base pairing) or by Watson/Crick base pairing (in the presence of a recombinase enzyme). The oligonucleotide of the invention is modified by the covalent attachment of one or more electrophilic groups. When a modified oligonucleotide is bound to its target sequence, the electrophilic group is able to interact with a nearby nucleotide in the target sequence, causing a modification to the nucleotide that results in a change in nucleotide sequence. Compositions used in the practice of the method are also disclosed.

22 Claims, 2 Drawing Sheets

OTHER PUBLICATIONS

Grigoriev et al., "Inhibition of gene expression by triple helix–directed DNA cross–linking at specific sites" *Proc. Natl. Acad. Sci. USA* 90:3501–3505 (1993).

Havre et al., "Targeted mutagenesis of DNA using triple helix–forming oligonucleotides linked to psoralen" *Proc. Natl. Acad. Sci. USA* 90:7879–7883 (1993).

Takasugi et al., "Sequence–specific photo–induced cross–linking of the two strands of double–helical DNA by a psoralen covalently linked to a triple helix–forming oligonucleotide" *Proc. Natl. Acad. Sci. USA* 88:5602–5606 (1991).

"Antisense Update: Keep your chin up" *Genesis Report* (Jun. 1993) 2(4) (Genesis Group Associates, Inc., 1993) (Abstract).

Agrawal et al., "Site specific functionalization of oligonucleotides for attaching two different reporter groups" *Nucleic Acids Res.* (1990) 18(18):5419–5423.

Brown, T. et al., "Modern machine–aided methods of oligodeoxyribonucleotide synthesis" in *Oligonucleotides and Analogues: A practical approach* ed. F. Eckstein, IRL Press, Oxford, 1991, pp. 1–24.

Crooke, "Editorial. Progress in evaluation of the potential of antisense technology" *Antisense Research and Development* (1994) 4:145–146.

Kessler, *Nonradioactive Labeling and Detection of Biomolecules,* C. Kessler, ed., Springer–Verlag, Berlin, 1992, pp. 13–14. (Title page also included herewith).

Maher, "DNA triple–helix formation: An approach to artificial gene repressors" *BioEssays* (1992) 14(12):807–815.

Matthews et al., "Review. Analytical strategies for the use of DNA probes" *Analyt. Biochem.* (1988) 169:1–25.

Pieles et al., "Preparation of a novel psoralen containing deoxyadenosine building block for the facile solid phase synthesis of psoralen–modified oligonucleotides for a sequence specific crosslink to a given target sequence" *Nucleic Acids Res.* (1989) 17(22):8967–8978.

Podyminogen et al., "Sequence specific covalent modification of DNA by cross–linking oligonucleotides. Catalysis by RecA and implication for the mechanism of synaptic joint formation" *Biochemistry* (1995) 34:13098–13108.

Praseuth et al. "Sequence–specific binding and photo-crosslinking of α and β oligodeoxynucleotides to the major groove of DNA via triple–helix formation" *Proc. Natl. Acad. Sci. USA* (1988) 85:1349–1353.

Sats et al., "Complementary addressed elimination of Ela–Sequences of SA7 simian adenovirus oncogen from ring–shaped single–strand DNA of M13 recombinant phages" *Bioorganicheskaya khimiya* (1988) 14(9):1188–1196. (Translation included herewith).

Singh et al., "Synthesis, characterization and conformational studies of the oligonucleotide 5'-CGCYCGGCATG–3' containing the modified base 1,$N^2$–propano–2' deoxyguanosine" *Abstr. Pap. Am. Chem. Soc.* (Apr. 1991) 201 (1–2). Abstract No. 364.

Stull and Szoka, Jr., "Antigene, ribozyme and aptamer nucleic acid drugs: Progress and prospects" *Pharmaceutical Research* (1995) 12(4):465–483.

Yamana et al., "Synthesis and interactive properties of an oligonucleotide with anthraquinone at the sugar fragment" *Bioconjugate Chem.* (1990) 1(5):319–324.

Arrand, "Preparation of Nucleic Acid Probes" Nucleic Acid Hybridisation, A Practical Approach, Hames and Higgins, eds., IRL Press, pp. 17–45 (1985).

Baker, B. R., "Design of Active–Site Directed Irreversible Enzyme Inhibitors" John Wiley and Sons, Inc., New York (1967).

Bergstrom, D., et al., "C–5 substituted pyrimidine nucleosides. 2. Synthesis via olefin coupling to organopalladium intermediates derived from uridine and 2'-deoxyuridine" J. Amer. Chem. Soc. vol. 100, No. 26, pp. 8106–8112 (1978).

Bigge, C., et al., "Palladium–catalyzed coupling reactions of uracil nucleosides and nucleotides" J. Amer. Chem. Soc. vol. 102, No. 6, pp. 2033–2038 (1980).

Blake, et al., "Hybridization arrest of globin synthesis in rabbit reticulocyte lysates and cells by oligodeoxyribonucleoside methylphosphonates" Biochemistry, vol. 24, pp. 6139–6145 (1985).

Bolli M et al., "Watson–Crick base–pairing properties of bicyclo–DNA" Nucleic Acids Res. 24: 4660–4667 (1996).

Busso, Mariano, "Nucleotide Dimers Suppress HIV Expression In Vitro" AIDS Research and Human Retroviruses, vol. 4, No. 6, pp. 449–455 (1988).

Calabresi P and Chabner BA, "Chemotherapy of Neoplastic Diseases" The Pharmacological Basis of Therapeutics, 8th Ed. (Gilman et al., eds.) Pergamon Press, New York, 1990, pp. 1202–1263.

Camerini–Otero, Rafael D. et al., "Method of Forming three Stranded DNA" Washington D.C.,: (U.S.) National Institutes of Health, Bethesda, Maryland. Nov. 9, 1990 (PB91–145581).

Chatterjee, Moneesh, et al., "Inducible Alkylation of DNA using an Oligonucleotide–Quinone Conjugate" J. Am. Chem. Soc., 1990, vol. 112, pp. 6397–6399.

Cheng, Suzanne, et al., "Use of psoralen–modified oligonucleotides to trap three stranded RecA–DNA complexes and repair of these cross–linked complexes by ABC excinuclease." J. Biol. Chem. 263:15,110–15,117 (1988).

Dale, R. et al., "The synthesis and enzymatic polymerization of nucleotides containing mercury: Potential tools for Nucleic Acid sequencing and structural analysis" Proc. Natl. Acad. Sci. USA vol. 70, No. 8, pp. 2238–2242 (1973).

Dale, R. et al., "Direct covalent mercuration of nucleotides and polynucleotides" Biochemistry vol. 14, No. 11, pp. 2447–2457 (1975).

De Clercq, E. et al., "Antiviral activity of 5–[(methylthio)methyl]–2'-deoxyuridine and other 5–substituted 2'-deoxyuridines." Biochem. Pharmacol. 28:3249–3254 (1979); Chemical Abstracts 92: 174218s (1980).

Demidov VV et al., "Kinetics and mechanism of polyamide ('peptide') nucleic acid binding to duplex DNA" Proc. Natl. Acad. Sci. USA 92:2637–2641 (1995).

Elsner H et al., "Photochemical crosslinking of protein and DNA in chromatin" Anal. Biochem. 149:575–581 (1985).

Fieser et al., "Reagents for Organic Synthesis" John Wiley and Sons, New York, vol. 1, pp. 837–841 (1967).

Friefelder, D., "Fluorescence spectroscopy" Physical Biochemistry, W.H. Freeman & Co., pp. 537–542 (1982).

Gall, J. et al., "Formation and detection of RNA–DNA hybrid molecules in cytological preparations" Proc. Natl. Acad. Sci., USA, vol. 63, pp. 378–383 (1969).

Gamper, et al., "Reverse southern hybridization" Nucleic Acids Res., vol. 14, No. 24, pp. 9943–9954 (1986).

Gibson, KJ et al., "Synthesis and application of derivatizable oligonucleotides" Nucleic Acids Research 15:6455–6467 (1987).

Glass RE, "Gene Function: *E. coli* and its heritable elements" University of California Press, Berkeley, CA, 1982, pp. 268–312.

Goodman, L. et al., "Chemical syntheses and transformations of nucleosides" Basic Principles in Nucleic Acid Chemistry (ed. P. Ts'o et al.,) vol. 1, Academic Press, New York, pp. 116–117 (1974).

Green, et al., "The Role of Antisense RNA in Gene Regulation" Ann. Rev. Biochem., vol. 55, pp. 569–597 (1986).

Hartley, J. et al., "Effect of ionic strength and cationic DNA affinity binders on the DNA sequence selective alkylation of guanine N7–positions by nitrogen mustards" Biochemistry, vol. 29, No. 12, pp. 2985–2991 (1990).

Hastie, et al., "Analysis of mRNA populations by cDNA–mRNA hybrid–mediated inhibition of cell–free protein synthesis" Proc. Nat'l Acad. Sci., vol. 75, No. 3, pp. 1217–1221 (1978).

Havre PA et al., "Targeted mutagenesis of Simian Virus 40 DNA mediated by a triple helix–forming oligonucleotide" J. Virology 67:7324–7331 (1993).

Hecht, et al., "Synthesis and biological activity of pyrazolo [3,4–d] pyrimidine nucleosides and nucleotides related to tubercidin, toyocamycin, and sangivamycin" Biochemistry, vol. 15, No. 5, pp. 1005–1015 (1976).

Hobbs, Frank, "Palladium–Catalyzed Synthesis of Alkynylamino Nucleosides. A Universal Linker for Nucleic Acids" J. Org. Chem. 54:3420–3422 (1989).

Iverson, Brent L. et al., "Nonenzymatic sequence specific methyl transfer to single stranded DNA" Proc. Natl. Acad. Sci. U.S.A., vol. 85, pp. 4615–4619 (1988).

John, H. et al., "RNA–DNA hybrids at the cytological level" Nature, vol. 223, pp. 582–587 (1969).

John, Rainer et al., "Synthese von sieben–und achtring–anellierten pyridinen durch 'inverse' intramolekulare diels–alder–reaktion mit trifluormethyl–substituierten 1,2, 4–Triazinen" Chem. Ber., vol. 123, pp. 133–136 (1990).

Jones, Roger A., "Preparation of Protected Deoxyribonucleotides" Oligonucleotide synthesis, Practical Approach Series, (ed M.J. Gait) IRL Press, Chapter 2, pp. 23–34 (1984).

Kido M et al., "*Escherichia coli* recA protein modified with a nuclear location signal binds to chromosomes in living mammalian cells" Exp. Cell Res. 198:107–114 (1992).

Knorre, D.G. et al., "Oligonucleotides linked to reactive groups" Oligonucleotides, Antisense Inhibitors of Gene Expression (JS Cohen, ed), CRC Press Chapter 8, pp. 173–196 (1989).

Knorre D.G. et al., "Complementary–Addressed (Sequence Specific) Modification of Nucleic Acids" Progress in Nucleic Acid Research and Molecular Biology, vol. 32, 1985, pp. 291–320.

Knorre D. G. et al., "Complementarily addressed modification of double–stranded DNA in a triple–stranded complex" Dokl. Akad. Nauk SSSR (Biochem.) 300:1006–1009 (1988).

Kobayashi, S., "The synthesis and xanthine oxidase inhibitory activity of pyrazolo [3,4–d] pyrimidines" Chem. Pharm. Bull., vol. 21, No. 5, pp. 941–951 (1973).

Kochetkov et al., Organic Chemistry of Nucleic Acids, Part B. (NK Kochetkov & El Budovskii, eds.) Plenum Press, New York. p. 375 (1972).

Kong, X–B, et al., "Topoisomerase II–mediated DNA cleavage activity and irreversibility of cleavable complex formation induced by DNA intercalator with alkylating capability" Molecular Pharmacology, vol. 41, pp. 237–244, 1992.

Langer, P. et al., "Enzymatic synthesis of biotin–labeled polynucleotides: Novel nucleic acid affinity probes" Proc. Natl. Acad. Sci. USA, vol. 78, No. 11, pp. 6633–6637 (1981).

Le Doan, Trung, et al., "Sequence–specific recognition, photocrosslinking and cleavage of DNA double helix by an oligo–[α]–thimidylate covalently linked to an azidoproflavine derivative" Nucleic Acids Research, vol. 15, No. 19, pp. 7749–7760 (1987).

Lee JS et al., "Coralyne binds tightly to both T–A–T and C–G–C+ containing DNA triplexes" Biochemistry 32:5591–5597 (1993).

Lin AJ et al., "Potential bioreductive alkylating agents," 'Cancer chemotherapy' (ed. Sartorelli AC) Amer. Chem. Soc., Washington, DC, 1976, pp. 71–75.

Lukhtanov EA et al., "Rapid and efficient hybridization–triggered crosslinking within a DNA duplex by an oligodeoxyribonucleotide bearing a conjugated cyclopropapyrroloindole" Nucleic Acids Res. 24:683–687 (1996).

Marchand C et al., "Stabilization of triple–helical DNA by a benzopyridoquinoxaline intercalator." Biochemistry 35:5022–5032 (1996).

Maxam, et al., "A new method for sequencing DNA" Proc. Nat'l Acad. Sci. USA, vol. 74, No. 2, pp. 560–564 (1977).

Meyer, Rich B. et al., "Efficient, Specific Cross–Linking and Cleavage of DNA by Stable, Synthetic Complementary Oligodeoxynucleotides" J. Am. Chem. Soc., vol. 111:8517–8519 (1989).

Milligan J et al., "Current concepts in antisense drug design" J. Med. Chem. 36(14):1923–1937 (1993).

Moser, H. et al., "Sequence–specific cleavage of double helical DNA by triple helix formation" Science, vol. 238, pp. 645–650 (1987).

Nielsen PE et al., "Sequence–selective recognition of DNA by strand displacement with a thymine–substituted polyamide." Science 254: 1497–1500 (1991).

Orson, Frank M. et al., "Oligonucleotide inhibition of IL2Rα mRNA transcription by promoter region colinear triplex formation in lymphocytes" Nucleic Acids Research, vol. 19., No. 12. May 17, 1991, pp. 3435–3441.

Pardue, "In Situ Hybridisation" Nucleic Acid Hybridisation, A Practical Approach, Hames and Higgins, eds., IRL Press, pp. 179–202 (1985).

Parris CN et al., "A signature element distinguishes sibling and independent mutations in a shuttle vector plasmid." Gene 117:1–5 (1992).

Paterson, et al., "Structural gene identification and mapping by DNA–mRNA hybrid–arrested cell–free translation" Proc. Nat'l Acad. Sci. USA, vol. 74, No. 10, pp. 4370–4374 (1977).

Petrie, CR et al., "A novel biotinylated adenylate analogue derived from pyrazolo[3,4–d]pyrimidine for labeling DNA probes" Bioconjugate Chem. 2:441–446 (1991).

Pieper, Russel O. et al., "Transcription Terminating Lesions induced by bifunctional alkylating agents in vitro" Carcinogenesis, vol. 10, No. 7, pp. 1307–1314 (1989).

Register, et al., "Electron Microscopic visualization of the RecA Protein Mediated Pairing and Branch Migration Phases of DNA Strand Exchange" J. Biol. Chem,., vol. 262, No. 26, pp. 12812–12820 (1987).

Robins, Morris J. et al., "Nucleic acid related compounds. 39. Efficient conversion of 5–iodo to 5–alkynyl and derived 5–substituted uracil bases and nucleosides" J. Org. Chem., vol. 48, pp. 1854–1862 (1983).

Robins, Morris J. et al., "Nucleic acid related compounds. 38. Smooth and high–yield iodination and chlorination at C–5 of uracil bases and p–toluyl–protected nucleosides" Can. J. Chem., vol. 60, pp. 554–557 (1982).

Ruth, J. et al., "C–5 substituted pyrimidine nucleosides.1. Synthesis of C–5 allyl, propyl, and propenyl uracil and cytosine nucleosides via organopalladium intermediates" J. Org. Chem., vol. 43, No. 14, pp. 2870–2876 (1978).

Salganik RI et al., "Gene–directed mutagenesis in bacteriophage T7 provided by polyalkylating RNAs complementary to selected DNA sites" Proc. Natl. Acad. Sci. USA 77: 2796–2800 (1980).

Sats, NV et al., "Complementary addressed elimination of the E1A region of the simian adenovirus SA7 oncogene from circular single stranded DNA of M13 recombinant phages" Bioorg. Khim.(Bioorganic Chemistry), vol. 14, No. 9, pp. 1188–1196 (1988) Abstract Only.

Seela, et al., "8–Aza–7–deaza–2'–deoxyguanosine: Phosphoramidite synthesis and properties of octanucleotides" Helv. Chim. Acta., vol. 71, pp. 1191–1198 (1988).

Seela, et al., "8–Aza–7–deazaadenine $N^8$–and $N^9$–(β–D–2'–Deoxyribofuranosides): Building blocks for automated DNA synthesis and properties of oligodeoxyribonucleotides" Helv. Chim. Acta., vol. 71, pp. 1813–1823 (1988).

Seela, et al., "Phosphoramidites of base–modified 2'–deoxyinosine isoteres and solid–phase synthesis of d(GCI*CGC) oligomers containing an ambiguous base" Nucleic Acids Research, vol. 14, No. 4, pp. 1825–1844 (1986).

Seela, F et al., "Poly(adenylic acids) containing the antibiotic tubercidin—base pairing and hydrolysis by nuclease S1" Nucleic Acids Res. 10: 1389–1397 (1982).

Seidman MM et al., "A shuttle vector plasmid for studying carcinogen–induced point mutations in mammalian cells" Gene 38:233–237 (1985).

Shaw, Jeng–Pyng, et al., "Specific, High–Efficiency, Triple–Helix–Mediated Cross–Linking to Duplex DNA" J. Am. Chem. Soc., 1991, vol. 113, pp. 7765–7766.

Sidwell RW et al., "In vivo antiviral properties of biologically active compounds. II: Studies with Influenza and Vaccinia viruses" Appl. Microbiol. 16:370–392 (1968).

Sinha, et al., "The preparation and application of functionalised synthetic oligonucleotides: III. Use of H–phosphonate derivatives of protected amino–hexanol and mercapto–propanol or –hexanol" Nucleic Acids Research, vol. 16, No. 6, pp. 2659–2669 (1988).

Sinha, N. et al., "Polymer support oligonucleotide synthesis XVIII: use of β–cyanoethyl–N, N–dialkylamino–/N–morpholino phosphoramidite of deoxynucleosides for the synthesis of DNA fragments simplifying deprotection and isolation of the final product" Nucleic Acids Research, vol. 12, No. 11, pp. 4539–4557 (1984).

Sonenberg, N et al., "Reovirus mRNA can be covalently crosslinked via the 5' cap to proteins in initiation complexes" Proc. Natl. Acad. Sci. USA 74:4288–4292 (1977).

Sonveaux, E., "The organic chemistry underlying DNA synthesis" Bioorgan. Chem, vol. 14, No. 3, pp. 274–325 (1986); Chemical Abstracts 107:59329v.

Stein, C. et al., "Antisense oligonucleotides as therapeutic agents–is the bullet really magical?" Science, vol. 261, pp. 1004–1012 (1993).

Stephenson, Mary L. et al., "Inhibition of Rous Sarcoma viral RNA translation by a specific oligodeoxyribonucleotide" Proc. Natl. Acad. Sci. U.S.A. 75:285–288 (1978).

Summerton, James et al., "Sequence Specific CrossLinking Agents for Nucleic Acids" J. Mol. Biol., vol. 122, pp. 145–162 (1978).

Sun, J. et al., "Oligo [α]–deoxynucleotides covalently linked to an intercalating agent. Double helices with parallel strands are formed with complementary[β]–deoxynucleotides" Nucleic Acids Research, vol. 15, No. 15, pp. 6149–6158 (1987).

Telser, J. et al., "DNA Duplexes Covalently Labeled at Two Sites: Synthesis and Characterization by Steady–State and Time–Resolved Optical Spectroscopies" J. Am. Chem. Soc. 111:7226–7232 (1989).

Thoung, Nguyen Thanh, et al., "Chemical synthesis of natural and modified oligodeoxynucleotides" Biocheme 67:673–684 (1985).

Tijssen, P., "Practice and Theory of Enzyme Immunoassays" Laboratory Techniques in Biochemistry and Molecular Biology, v 15, Burdon R.H., van Knippenberg, P.H., eds., Elsevier, pp. 9–20 (1985).

Tseng BY, Brown KD, "Antisense oligonucleotide technology in the development of cancer therapeutics" Cancer Gene Therapy 1(1):65–71 (1994).

Turchinskii, MF et al., "Conversion of noncovalent interactions in nucleoproteins into covalent bonds." FEBS Letters 38:304–307 (1974).

Uhlmann E., Peyman, A, "Antisense Oligonucleotides: A New Therapeutic Principle" Chemical Reviews 90:543–584 (1990).

Umlauf, Scott W. et al., "Triple–helical DNA Pairing Intermediates Formed by recA Protein" J. Biol. Chem. 265: 16898–16912 (1990).

Vlassov V, et al., "Sequence–specific chemical modification of double–stranded DNA with alkylating oligodeoxyribonucleotide derivatives" Gene 72:313–322 (1988).

Webb, Thomas R. et al., "Hybridization triggered cross–linking of deoxyligonucleotides" Nucleic Acids Research, vol. 14, pp. 7661–7674 (1986).

Weiss, Rick, "Upping the antisense ante: Scientists bet on profits from reverse genetics" Science News, vol. 139, pp. 108–109 (1991).

Wilson WD et al., "DNA triple helix–specific intercalators as antigene enhancers: Unfused aromatic cations" Biochemistry 32: 10614–10621 (1993).

Zamecnik, Paul C. et al., "Inhibition of Replication and Expression of Human T–Cell lymphotrophic virus type III in cultured cells by exogenous synthetic oligonucleotides complementary to viral RNA" Proc. Nat'l Acad. Sci., U.S.A., vol. 83, Jun. 1986, pp. 4143–4146.

Zamecnik, Paul C. et al., "Inhibition of Rous sarcoma virus replication and cell transformation by a specific oligodeoxynucleotide" Proc. Nat'l Acad. Sci. USA, 75: 280–284 (1978).

"HOMOLOGOUS STRAND"

5'*...CTGCTCGAGCTCTGGTGGGGTTCCCGAGCGGCCAAAGGAGCAGACTCTAAATCTGCCGTCATCGACTTCGAAGGTTCGAATCCTTCCCCACCACCACGGCCGAAATTCGGTACCCGATCCT...3' pCTCGAGCTGTGGUGGGGTTCCCGAGCGGCC ODN2 SEQ ID NO:4  pTCTGCCGUCATCGACTTCGAAGGTTCGAATCCTUCCCCACCACCACGGC ODN7 SEQ ID NO:9 pCTCGAGCTGTGGTGGGGTUCCCGAGCGGCC ODN3 SEQ ID NO:5  pTCTGCCGTCATCGACTTCGAAGGTTCGAATCCTUCCCCACCACCACGGC ODN6 SEQ ID NO:8 pCTCGAGCTGTGGUGGGGTUCCCGAGCGGCC ODN1 SEQ ID NO:3

...GACGAGCTCGACACCACCCCAAGGGCTCGCCGGTTTCCCTCGTCTGAGATTTAGACGGCAGTAGCTGAAGCTTCCAAGCTTAGGAAGGGGTGGTGCCGGCTTTAAGCCATGGGCCTAGGA...5'*

3'

"COMPLEMENTARY STRAND"

U - CHLORAMBUCIL CONJUGATED THROUGH 5-(3-AMINOPROPYL) URIDINE p - 5' -HYDROXYPROPYL PHOSPHATE

FIG. 1

```
5' GAATTCGAGA GCCCTGCTCG AGCTGTGGTG                    GGGTTCCCGA                GCGGCCAAAG              GGAGCAGACT 3'
3' CTTAAGCTCT CGGGACGAGC TCGACACCAC                    CCCAAGGGCT                CGCCGGTTTC              CCTCGTCTGA 5'
                                   ↑ 5' tRNA START
                                         T                AA  GGA                  G                      AA    G
                                         T                CAA GGA                  A  AA   T A
                                         T                AT                       A
                                         T                AT                       A
                                         T                AT
                                         T                AT
                                         T                AG
                                         T                A
                                         T
                                         T
                                         AT
```

SUMMARY:
TOTAL NUMBER OF CLONES SEQUENCED: 76
TOTAL NUMBER OF POINT MUTATIONS: 49
TOTAL NUMBER OF DELETIONS: 13

FIG. 2

TARGETED MUTAGENESIS IN LIVING CELLS USING MODIFIED OLIGONUCLEOTIDES

CROSS-REFERENCE TO RELATED APPLICATIONS

This application is a continuation-in-part of U.S. patent application Ser. No. 08/485,611, filed Jun. 7, 1995 now U.S. Pat. No. 5,849,482, which is a continuation-in-part of application Ser. No. 08/178,733 filed on Jan. 7, 1994, now abandoned, which is a continuation of application Ser. No. 07/748,138 filed on Aug. 21, 1991, now abandoned, the disclosures of which are hereby incorporated by reference in their entirety.

TECHNICAL FIELD

This application is in the fields of site-directed mutagenesis and gene therapy. More particularly, it is in the field of site-directed mutagenesis in living cells using oligonucleotides with attached electrophilic groups, that are capable of forming a three-stranded structure with a target double-stranded DNA molecule.

BACKGROUND ART

"Antisense" technology encompasses the use of sequence-specific oligonucleotides (ODNs) to bind to mRNA and inhibit its function. A variation of the "antisense" approach to rational drug design is termed "anti-gene". Whereas antisense ODNs target single stranded mRNA, anti-gene ODNs hybridize with and are capable of inhibiting the function of double-stranded DNA. More specifically, anti-gene ODNs form sequence-specific triple-stranded complexes with a double stranded DNA target and thus may affect the replication or transcription of selected target genes. As is known, except for certain RNA viruses and nucleic acid-free viroids (and possibly prions), DNA is the repository for all genetic information, including regulatory control sequences and non-expressed genes, such as dormant proviral DNA genomes. In contrast, the target for antisense ODNs, mRNA, represents a very small subset of the information encoded in DNA. Furthermore, for a given gene, the mRNA transcript is present at a much higher effective concentration than the DNA which encodes the transcript. Anti-gene ODNs are, therefore, effective in much lower concentrations than antisense ODNs. Thus, anti-gene ODNs have broader applicability and are potentially more powerful than antisense ODNs that merely inhibit mRNA processing and translation.

Anti-gene ODNs in the nuclei of living cells can form sequence-specific complexes with chromosomal DNA. The resultant triplexes have been shown to inhibit restriction and/or transcription of the target double stranded DNA. Based on the known stabilities of the two target nucleic acid species (i.e., DNA and RNA), anti-gene interference with DNA functioning has longer lasting effects than the corresponding antisense inhibition of mRNA function.

As noted above, anti-gene therapy is based on the observation that under certain conditions DNA can form triple-stranded complexes. Several forms of triple-strand complex are known. In one type of triple-stranded complex, the third strand resides in the major groove of the Watson-Crick base paired double helix, where its hydrogen bonds to one of the two parental strands. A binding code governs the recognition of base pairs by a third base (see allowed triplets below, Hoogsteen or reverse Hoogsteen pairing). In each case, the third strand base is presented first (in boldface) and is followed by the base pair in the Watson-Crick duplex.

allowed triplets:
  A-A-T G-G-C
  T-A-T C-G-C

Certain limitations of this base pair recognition code are apparent from the allowed triplets. First, there is no capability for the recognition of T-A and C-G base pairs; hence, triple strand formation is restricted to runs of purine bases on one strand and pyrimidine bases on the other strand of the duplex. In other words, the third strand or ODN binds only to one strand of the duplex and can only bind to purines. Second, if cytosine ("C") is in the third strand, it must be protonated to be able to hydrogen bond to the guanine of a G-C base pair. The $pK_a$ for protonation of cytosine is 4.6, suggesting that at physiological pH the stability of C-G-C triads is likely to be impaired. Third, in all cases triads are maintained by two hydrogen bonds between the third strand base and the purine residue of the duplex base pair. Hence, triple-stranded complexes are generally less stable than the parental double-stranded DNA, which is maintained by a combination of two (A-T) or three (G-C) hydrogen bonds between purine and pyrimidine pairs. (Watson-Crick motif).

An important disadvantage of triple strand formation as discussed above is the relatively slow kinetics of triple strand formation. However, triple strand formation can be catalyzed in cells by recombinase enzymes which are practically ubiquitous in cells and whose existence is well known in the art. In addition to a much faster rate of triple strand formation, recombinase enzyme-catalyzed triple strand formation also provides the advantage of universal sequence recognition (in contrast to the A-T and G-C recognition limitation associated with non-enzyme-mediated triple strand formation). More specifically, the recombinase enzyme-mediated recognition motif recognizes all four base pairs, thereby allowing targeting of any double stranded DNA sequence. Second, the nucleoprotein filament, which is the complex formed between a recombinase enzyme and the single-stranded ODN, searches for target double strand DNA homology much more efficiently than does a small naked anti-gene ODN, thus decreasing the concentration of anti-gene ODN required for efficient triple strand complex formation. Third, due to the hydrogen bonding patterns, the resultant triple strand complex is stable at physiological pH. Fourth, since cellular recombination mechanisms are being utilized, the DNA in higher order chromatin structures is accessible for targeting.

The ability to achieve targeted mutagenesis of a chromosomal gene in a living cell is a long-sought goal in the area of gene therapy. In its most effective embodiment, targeted mutagenesis would result in the change of a single nucleotide in the sequence of a chromosomal gene, for example conversion of a point mutant allele into its wild-type counterpart, or inactivation of a deleterious gene by creating a nucleotide triplet specifying translational termination. In order to direct mutagenizing agents to a particular target nucleotide sequence, a targeting mechanism having high specificity is required. Such specificity can be obtained, for a polynucleotide target, by the use of a synthetic oligonucleotide having a sequence that allows the oligonucleotide to bind to the target sequence.

Binding of an oligonucleotide to a single-stranded target can be accomplished by designing the sequence of the oligonucleotide such that it base-pairs with its target, in the Watson-Crick sense. However, it is also possible to design an oligonucleotide with a sequence that will allow it to base-pair with a duplex nucleic acid, forming a triple-stranded nucleic acid, or triplex. Fresco, U.S. Pat. No. 5,422,251. Attachment of a suitable modifying agent to such an oligonucleotide would make it possible to generate a lesion at or near a target sequence in a gene of interest. Subsequent cellular processes related to DNA replication and/or repair can result in either restoration of the original sequence by repair of the lesion, or mutagenesis, for example by misrepair, resulting in a base change at the site of the lesion.

Despite numerous attempts to develop appropriate reagents and techniques, generation of a specific mutation in a chromosomal gene by a modified oligonucleotide has yet to be demonstrated. Indeed, consideration of the possible consequences of targeted damage to the genome of a cell by a modified oligonucleotide suggests that more likely outcomes of such damage would be either cell death or regeneration of the original sequence. For instance, the presence of a low level of a specific type of damage at a particular site (as can occur when mutation is targeted to a specific site, for example, by the use of an oligonucleotide) might be expected to be readily corrected by cellular repair mechanisms. On the other hand, widespread damage at multiple sites might be anticipated to overwhelm the repair capacity of the cell, resulting in the accumulation of multiple mutations in a variety of genes and consequent cell death.

Attempts to exploit the specificity of RNA-DNA base-pairing to direct the targeting of mutagenic agents in vitro were conducted by Salganik et al. (1980) *Proc. Natl. Acad. Sci. USA* 77:2796–2800. In these experiments, a heterobifunctional alkylating agent was attached to mRNA transcripts of bacteriophage T7, at random locations within the transcripts. These modified mRNAs were capable of hybridization to T7 DNA, albeit at a lower efficiency than unmodified mRNA. Following hybridization of these modified mRNAs to T7 DNA, activation of the alkylating group by reduction, and packaging of the modified DNA, a low frequency of mutations was detected in progeny phage, as measured by plating efficiency on various indicator strains of the host bacterium *Escherichia coli*.

Although pioneering for its time, this method did not allow efficient targeting of mutational events to a particular nucleotide in a living cell. First, it was not possible to place the mutagenic alkylating group at a specific site on the modified mRNA. Therefore, site-specific mutagenesis of the target sequence was not possible. Second, modification of the mRNA reduced its efficiency of hybridization to its target. Third, hybridization was performed in vitro under R-loop conditions, which favor RNA-DNA hybridization. Finally, after hybridization of the modified mRNA to its target, activation of the mutagenic alkylating group by sodium borohydride reduction was required. These last two factors make the method unsuitable for use in living cells.

Others have demonstrated mutagenesis of a target sequence after binding of a modified triplex-forming oligonucleotide to a target ex vivo, or in vitro followed by transfection into mammalian cells, where the target DNA was assumed to undergo replication and/or repair. Glazer, PCT publication WO 95/01364. The oligonucleotides exemplified in these experiments were modified by the attachment of a psoralen, a photoactivatible crosslinking agent. However, the utility of such photoactivatible crosslinkers for targeted mutagenesis in living cells is limited, for several reasons. First, in order to obtain crosslinking, which appears to be a necessary prerequisite for mutagenesis, the triplex formed by the modified oligonucleotide must be exposed to near ultraviolet light. Since near ultraviolet light will not penetrate the skin, psoralen-modified oligonucleotides are not useful for mutagenesis in cells of internal organs or in other regions of the body not penetrable by near ultraviolet light.

A second problem associated with attempts to use psoralen-modified oligonucleotides for targeted mutagenesis in living cells derives from the fact that formation of triplexes is an equilibrium process, such that binding of a triplex-forming oligonucleotide to its target sequence is reversible. Hence, at any given moment, a certain fraction of mutagenic oligonucleotides are bound in triplexes with target and a certain fraction remain unbound. When the photoactivatible triplex-forming oligonucleotides of the prior art are illuminated to induce crosslink formation, only those oligonucleotides bound to their target at the moment of illumination will form crosslinks which have the potential to generate a mutation. Thus, in order to obtain maximal degrees of mutagenesis, either constant irradiation of cells with near ultraviolet light, or extremely high occupancy of binding sites (that is not characteristic of the binding equilibrium between modified oligonucleotide and target sequence) would be required.

A third problem with the potential use of psoralen-modified oligonucleotides for targeted mutagenesis of living cells is that the ultraviolet irradiation required for activation of the psoralen group is likely to have nonspecific adverse effects on cellular macromolecules. For instance, ultraviolet irradiation will induce the formation of thymine dimers in DNA, which would likely lead to nonspecific generation of mutations outside of the target site. Alternatively, or in addition to its effects on DNA, ultraviolet light can cause protein crosslinking, which could lead to various types of cellular malfunction or cell death.

A fourth problem is that psoralen itself has a non-specific affinity for DNA. As a result, a high proportion of lesions are expected to occur at sites other than the target site when psoralen-containing agents are used.

Hence, there remains a great deal of uncertainty regarding the ability of modified oligonucleotides to cause specific, non-lethal nucleotide sequence changes in the genome of a living cell. To make practical the targeted mutagenesis of a gene in a living cell, it would be necessary to develop an agent which is capable of specific interaction with a target double-stranded nucleotide sequence, and which has an intrinsic ability to react with genomic DNA (i.e., does not require external activation) in the nucleus of a cell.

All patents and publications mentioned herein, either supra or infra, are hereby incorporated by reference in their entirety.

DISCLOSURE OF THE INVENTION

The present invention provides a method for obtaining a targeted mutation at a specific nucleotide sequence in a living cell. The invention further encompasses compositions for use in the claimed methods. Compositions of the invention include a modified oligonucleotide comprising an electrophilic group covalently attached to an oligonucleotide capable of sequence-specific interaction with a target sequence in a double-stranded DNA molecule. The electrophilic group(s) can be attached at one or more specific sites on the oligonucleotide, and are inherently capable of reacting with target functional groups. The interaction between the modified oligonucleotide and the double-stranded target sequence can take the form of triplex formation, wherein bases in the modified oligonucleotide interact with bases in the double-stranded target by Hoogsteen or reverse Hoogsteen base-pairing (or the equivalent) to form a triple-stranded nucleic acid. Alternatively, the modified oligonucleotide, in combination with a recombinase enzyme, can bind to one strand of a duplex DNA by Watson/Crick base-pairing.

The modified oligonucleotides of the invention typically include a linker arm (such as an alkyl, alkoxy, aminoalkyl or amidoalkyl chain) and an electrophilic reactive group. After complex formation with the target sequence, the modified oligonucleotide is capable of reacting with the target DNA to form a covalent bond therewith. As a result of covalent bond formation between the modified ODN and the target sequence, replication and/or expression of the target sequence can be affected in such a way as to cause a heritable alteration in one or more nucleotides of the target sequence.

The ODNs of the present invention, in addition to having a covalently attached electrophilic agent, can also have other modifications, such as modifications of the heterocyclic bases, of the sugar as well as of the phosphate moieties, relative to naturally occurring ribonucleotides and deoxyribonucleotides. The electrophilic agents can be attached to either the heterocyclic bases, to the sugars or modified sugars, or to the phosphate or modified phosphate moieties.

In one embodiment, the present invention provides a method for site-directed mutagenesis of a target sequence in a double-stranded DNA molecule, said double-stranded DNA molecule residing in a cell capable of replicating said double-stranded DNA molecule, said target sequence comprising a sequence of nucleotides, said method comprising the steps of:

a) contacting said double-stranded DNA molecule with an oligonucleotide comprising one or more electrophilic groups, wherein the oligonucleotide and the double-stranded DNA molecule form a three-stranded complex in the region of the target sequence;

b) allowing reaction to occur between an electrophilic group and a nucleotide in the target sequence to generate one or more chemically modified sites; and c) allowing the double-stranded DNA molecule comprising one or more chemically modified sites to undergo one or more rounds of replication, thereby generating one or more mutations at or in the vicinity of the target sequence.

In another embodiment, the invention provides a method of inducing a mutation in a target polynucleotide sequence, said target polynucleotide sequence comprising a sequence of nucleotides, said method comprising:

contacting said target polynucleotide sequence with a sequence-specific oligonucleotide to which is covalently attached one or more electrophilic groups; and allowing reaction to occur between one of said electrophilic groups and one of said nucleotides, thereby resulting in a mutation in the target polynucleotide sequence.

BRIEF DESCRIPTION OF THE DRAWINGS

FIG. 1 shows the nucleotide sequence of a portion of the pSP189 plasmid containing the supF suppressor tRNA gene. Also shown are the sequences of several modified oligonucleotides used for mutagenesis of the target sequence, aligned with the plasmid sequence.

FIG. 2 shows the spectrum of mutations obtained in the supF gene region of the pSP189 plasmid following reaction with the modified oligonucleotides of the invention. The bottom two lines show the sequences of both strands of the gene; lines above this show changes in the sequence induced by the modified oligonucleotides of the invention. Sequences of the mutants are identical to that of the wild-type gene, except where indicated.

BEST MODE FOR CARRYING OUT THE INVENTION

Definitions

An oligonucleotide (ODN) is a nucleic acid polymer comprising a plurality of nucleotide subunits of defined base sequence. Generally, an oligonucleotide is shorter than 3000 nucleotides in length, preferably, shorter that 150 nucleotides, more preferably shorter than 75 nucleotides and, most preferably, 50 nucleotides or shorter. Oligonucleotides comprise a chain of nucleotides which are linked to one another by phosphate ester linkages. Each nucleotide typically comprises a heterocyclic base (nucleic acid base), a sugar moiety attached to the heterocyclic base, and a phosphate moiety which esterifies a hydroxyl function of the sugar moiety. The principal naturally-occurring nucleotides comprise uracil, thymine, cytosine, adenine and guanine as the heterocyclic bases, and ribose or deoxyribose as the sugar moiety. Modified bases, sugars and/or phosphate moieties, as are known in the art, are also useful in the oligonucleotides of the present invention.

A sequence-specific oligonucleotide is an oligonucleotide that is capable of binding to a target sequence, either through Watson/Crick base-pairing (optionally in the presence of a recombinase), or through triplex formation (for example by Hoogsteen or reverse Hoogsteen base pairing or the equivalent) to form a three-stranded nucleic acid structure.

A target sequence is a nucleotide sequence in a polynucleotide of interest, in which it is desired to induce a mutation using the methods of this invention.

A mutation is a change in the nucleotide sequence of a gene. Said change can, for instance, take the form of a substitution of one nucleotide for another, insertion of one or more nucleotides, deletion of one or more nucleotides, duplication of a particular stretch of nucleotide sequence, or a change in the arrangement of nucleotides in a sequence such as inversion or translocation.

A mutagen is an agent capable of causing a mutation.

An electrophilic group is a reagent or moiety that accepts an electron pair (from a nucleophilic group) to form a covalent bond.

A recombinase is an enzyme that is involved in recombination in either a procaryotic or a eucaryotic cell. Activities of recombinases include, but are not limited to, promoting the base-pairing of a single-stranded nucleic acid with a double-stranded nucleic acid, one of whose strands is complementary to the single-stranded sequence.

Triplex formation occurs when a single-stranded oligo- or polynucleotide binds to a double-stranded oligo- or polynucleotide to form a stable three-stranded structure in which each of the three strands interacts with one or more other strands by hydrogen bonding between the heterocyclic bases. The hydrogen bonding between the single-stranded polynucleotide and one of the strands of the duplex can, for example, be mediated by Hoogsteen base-pairing, reverse Hoogsteen base-pairing or an equivalent type of base-pairing.

A triplex-forming oligonucleotide is an oligonucleotide that is capable of forming a triple-stranded structure with a double-stranded oligo- or polynucleotide target wherein each of the three strands interacts with one or more other strands by hydrogen bonding between the heterocyclic bases. Hydrogen bonding between the triplex-forming oligonucleotide and the double-stranded target will generally occur within a polypurine stretch of seven or more nucleotides on one strand of the target duplex and will generally follow the rules of Hoogsteen or reverse Hoogsteen base-pairing or the equivalent. A limited number of pyrimidine interruptions in the polypurine stretch can be accommodated in the method of the invention.

Watson/Crick base pairing involves hydrogen-bonding between G and C residues and between A and T (or U). It is the type of base-pairing that normally occurs in chromosomal DNA.

A nitrogen mustard (or N-mustard) is a moiety comprising one or more leaving groups (typically chloride or fluoride), each attached by a short (preferably, two-carbon) chain to a basic nitrogen atom.

A triplex stabilizer is a molecule that interacts specifically with triple-stranded nucleic acid structures by stacking between the base triads in a triplex, thereby enhancing the stability of the triplex.

Method

In accordance with the broad principles of the present invention, at least one electrophilic group is attached to an oligonucleotide which is capable of binding to a target DNA sequence, as explained in detail below. The method of the invention comprises contacting a sequence-specific oligonucleotide containing an attached electrophilic group with a target nucleic acid sequence, to allow modification of the target sequence by the electrophilic agent.

The oligonucleotides of the invention can comprise ribonucleotides (containing ribose as the only or principal sugar component), deoxyribonucleotides (containing deoxyribose as the principal sugar component), or in accordance with established state-of-the-art, modified sugars or sugar analogs can be incorporated in the ODN of the present invention. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in a pyranosyl or in a furanosyl form. In the modified ODNs of the present invention the sugar moiety is preferably the furanoside of ribose, deoxyribose, arabinose, 2-fluoro-2-deoxyribose, 2-O-methylribose or 3-amino-2,3-dideoxyribose, and the sugar can be attached to the respective heterocyclic bases either in α or β anomeric configuration. The preparation of these sugars or sugar analogs and of the respective "nucleosides" wherein such sugars or analogs are attached to a heterocyclic base (nucleic acid base) per se is known, and need not be described here, except to the extent such preparation is provided here in connection with one or more specific examples. Preferably the sugar moiety is ribofuranose, 2-deoxyribofuranose or 2-fluoro-2-deoxyribofuranose in the β configuration.

The phosphorous derivative (or modified phosphate group) which can be attached to the sugar or sugar analog moiety in the modified oligonucleotides of the present invention can be a monophosphate, alkylphosphate, alkanephosphate, phosphorothioate, phosphorodithioate, phosphoramidate or the like. The preparation of the above-noted phosphate analogs, and their incorporation into nucleotides, modified nucleotides and ODNs, per se, is also known and need not be described here. Preferably, the phosphate derivative incorporated into the therapeutic oligonucleotides of the present invention is a "simple" phosphate, which in an internucleotide bond forms a phosphate diester, and which at the 3' and 5' ends of the modified ODNs of the invention can carry the electrophilic agent. In this regard it is noted that recombinase enzymes recognize such "simple" phosphates and deoxyribose backbones. The electrophilic agent is described in substantial detail below.

The heterocyclic bases, or nucleic acid bases which are incorporated in the modified ODNs of the present invention can be the naturally occurring principal purine and pyrimidine bases, (namely uracil, thymine, cytosine, adenine and guanine, as mentioned above), as well as naturally occurring and synthetic modifications of said principal bases. Those skilled in the art will recognize that a large number of "synthetic" non-natural nucleosides comprising various heterocyclic bases (and base analogues) and various sugar moieties (and sugar analogues) have become available in the prior art, and that as long as other criteria of the present invention (such as being "complementary" to a target sequence in the Watson Crick, Hoogsteen or reverse Hoogsteen sense, as applicable) are satisfied, the novel ODNs of the invention can include one or several heterocyclic bases other than the principal five base components of naturally occurring nucleic acids. Preferably, however, the heterocyclic base in the modified ODNs of the present invention is selected from thymine, uracil, cytosine, adenine, guanine, 4-aminopyrrolo[2,3-d]pyrimidine, 2-amino-4-oxopyrrolo[2,3-d]pyrimidine, 4-aminopyrazolo[3,4-d]pyrimidine or 4-amino-6-oxopyrazolo[3,4-d]pyrimidine groups, wherein the purines are attached to the sugar moiety of the oligonucleotides via the 9-position, the pyrimidines via the 1-position, the pyrrolopyrimidines via the 7-position and the pyrazolopyrimidines via the 1-position.

Also of use in the present invention are oligomers that are capable of forming triple-stranded complexes with a double-stranded nucleic acid target, but which may not necessarily comprise traditional nucleoside or nucleotide subunits, for example, peptide nucleic acids [Nielsen et al. (1991) *Science* 254: 1497–1500; and Demidov et al. (1995) *Proc. Natl. Acad. Sci. USA* 92:2637–2641] or bicyclo DNA oligomers [Bolli et al. (1996) *Nucleic acids Res.* 24: 4660–4667] or related structures.

The electrophilic agents incorporated in the present invention need to meet the requirements that (1) each electrophilic agent must be covalently bonded to a site on the ODN or be a component of a moiety, such as a linker arm, that is covalently bonded to a site on the ODN, (2) its length and steric orientation must be such that it can reach a suitable reaction site in the target sequence after the ODN is hybridized or complexed with the target (with or without the assistance of an enzyme), and (3) each electrophilic agent must comprise a reactive group which will react with a nucleophilic reactive group of the target sequence. As noted above, the electrophilic agents can be covalently attached to the heterocyclic bases or base analogues, the sugar or modified sugar residues, or the phosphate or modified phosphate functions of the ODNs (or be part of a moiety that is covalently attached to a base, sugar or phosphate function). Any covalent attachment of a single electrophilic agent (or the moiety of which it is a part) to the ODN and any combination of covalent attachment of two or more electrophilic agents (or two or more moieties each comprising an electrophilic group) to the ODN is within the broad scope of the present invention.

In one aspect of the invention, the electrophilic group can be part of a cross-linking agent. In the simplest terms the cross-linking agent comprises three groups or moieties, namely the reactive group E (which is typically and preferably an electrophilic group such as an electrophilic carbon), that carries a leaving group (L), and an "arm" (A), the electrophilic group E being attached to or being part of the arm A, which attaches the electrophilic group to the oligonucleotide. The leaving group L and/or leaving group-electrophilic group combination E-L can be chosen from, for example, such groups as chloro, bromo, iodo, $SO_2R'''$, or $S^+R'''R''''$, where each of R''' and R'''' is independently $C_{1-6}$ alkyl or aryl or R''' and R'''' together form a $C_{1-6}$ alkylene bridge. Chloro, bromo and iodo are preferred. Within these groups haloacetyl groups such as $—COCH_2I$, and bifunctional "nitrogen mustards", such as $—N—[(CH_2)_2—Cl]_2$ are preferred. The leaving group will be altered by its leaving ability. Depending on the nature and reactivity of the particular leaving group-electrophilic group combination, the groups to be used are chosen in each case to give the desired specificity of the irreversibly binding probes.

As noted above, the "arm" (or linker arm) A is a single entity which can include the electrophilic group or can covalently bond the ODN to the electrophilic group, and attaches the leaving group L, and maintains the electrophilic group-leaving group combination E-L at a desired distance and steric position relative to the ODN. Nevertheless, in practice the "arm" A can be constructed in a synthetic scheme where a bifunctional molecule is covalently linked to the ODN (for example by a phosphate ester bond to the 3' or 5' terminus, or by a carbon-to-carbon bond to a heterocyclic base) through its first functionality, and is also covalently linked through its second functionality (for example an amine) to a bridging moiety (alkyl bridge, alkylaryl bridge or aryl bridge, or the like) which, in turn, carries the electrophilic group-leaving group combination E-L.

A general formula of the cross linking function is thus -A-L, or $-A-L_2$ wherein L is the above defined leaving group and A is a moiety that is covalently linked to the ODN and which comprises the electrophilic group E. The A "arm" moiety itself should be unreactive (other than through the electrophilic group-leaving group combination E-L) under the conditions of interaction between the ODN and the target DNA sequence, and should maintain the electrophilic group-leaving group combination E-L in a desired steric position and distance from the desired site of reactions (such as an N-7 position of a guanosine residue or an N-3 position of an adenosine residue) in the target sequence. Generally speaking, the length of the A group should be equivalent in length to approximately 2 to 80 atoms, preferably 2 to 40 atoms.

An exemplary more specific formula for a class of preferred embodiments of the cross-linking function is $—(CH_2)_q—Y—(CH_2)_m-L$, where L is the leaving group, defined above, each of m and q is independently 0 to 8, inclusive, and where Y is defined as a "functional linking group". A "functional linking group" is a group that has two functionalities, for example $—NH_2$ and $—OH$, or $—COOH$ and $—OH$, or $—COOH$ and $—NH_2$, which are capable of linking the $(CH_2)_q$ and $(CH_2)_m$ bridges. An acetylenic terminus ($HC{\equiv}C—$) is also a suitable functionality as a precursor for Y, because it can be coupled to certain heterocycles and thereafter hydrogenated, as described below.

Other exemplary and more specific formulas for a class of preferred embodiments of the cross-linking function are $—(CH_2)_q—NH—CO—(CH_2)_m—(X)_n—N(R_1)—(CH_2)_p-L$ and $—(CH_2)_{q'}—O—(CH_2)_{q''}—NH—CO—(CH_2)_m—(X)_n—N(R_1)—(CH_2)_p-L$ where q, m and L are defined as above, q' is 3 to 7 inclusive, q'' is 1 to 7 inclusive, X is phenyl or simple substituted phenyl (such as chloro-, bromo-, lower alkyl- or lower alkoxy-substituted phenyl) or simple condensed phenyl (such as naphthyl or quinolinyl), n is 0 or 1, p is an integer from 1 to 6, and $R_1$ is H, lower alkyl or $(CH_2)_p-L$. Preferably p is 2. Those skilled in the art will recognize that the structure $—N(R_1)—(CH_2)_2-L$ describes a "nitrogen mustard", which is a class of potent alkylating agents. Particularly preferred within the scope of the present invention are those modified ODNs where the cross-linking agent includes the functionality $—N(R_1)—(CH_2)_2-L$ where L is halogen, preferably chlorine; and even more preferred are those modified ODNs where the cross linking agent includes the grouping $—N—[(CH_2)_2-L]_2$ ( a "bifunctional" N-mustard).

A particularly preferred partial structure of the cross linking agent includes the grouping

In a particularly preferred embodiment the just-noted cross-linking group is attached to an n-hexylamine-bearing tail at the 5' and 3' ends of the ODN in accordance with the following structure:

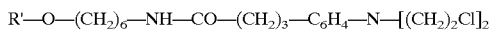

where R' signifies the terminal 5' or 3'-phosphate group of the ODN.

Other examples for the A-L group, particularly when attached to a heterocyclic base in the oligonucleotide (such as to the 5-position of 2'-deoxyuridine) are 3-iodoacetamidopropyl, 3-(4-bromobutyramido)propyl, 4-iodoacetamidobutyl and 4-(4-bromobutyramido)butyl groups.

In addition to the above-described groups which react with a nucleophilic site on the target DNA to bring about covalent attachment of the ODN to the target sequence, the ODNs of the invention can also have a psoralen moiety attached through an appropriate linker arm. Oligonulceotides carrying attached psoralen groups are described, for example, in Takasugi et al. (1991) *Proc. Natl. Acad. Sci. USA* 88:5602–5606, the disclosure of which is hereby incorporated by reference in its entirety. The above-described generic principles pertaining to the structure, synthesis and attachment of the linker arm to the ODN of the invention, as well as the state of the art pertaining to cross-linking with psoralen and related photo-crosslinking moieties, will enable one of ordinary skill in the art to make and use a modified ODN according to the present invention that has one or more psoralen or like moieties attached for crosslinking with a target sequence.

In accordance with other preferred embodiments, the cross-linking functionality is covalently linked to the heterocyclic base, for example to the uracil moiety of a 2'-deoxyuridylic acid building block of the ODN. The linkage can occur through the intermediacy of an amino group, that is, the "arm-leaving group combination" (A-L) can be attached to a 5-amino-2'-deoxyuridylic acid building unit of the ODN. The linkage via an amino group may be directly to the 5-position of the ring, or may, for example, be to an exocyclic group, such as a pyrimidine $N^4$ amino group. In still other preferred embodiments the "arm-leaving group combination" (A-L) is attached to the 5-position of the 2'-deoxyuridylic acid building unit of the ODN by a carbon-to-carbon bond. Generally speaking, 5-substituted-2'-deoxyuridines can be obtained by an adaptation of the general procedure of Robins et al. (1982) *Can. J. Chem.* 60:554–557; (1983) *J. Org. Chem.* 48:1854–1862. In accordance with this adaptation, the palladium-mediated coupling of a substituted 1-alkyne to 5-iodo-2'-deoxyuridine gives an acetylene-coupled product. The acetylenic deoxyuridine analog is reduced, with Raney nickel for example, to give the saturated compound, which is then used for direct conversion to a reagent for use on an automated DNA synthesizer. Examples of reagents which can be coupled to 5-iodo-2'-deoxyuridine in accordance with this scheme are:

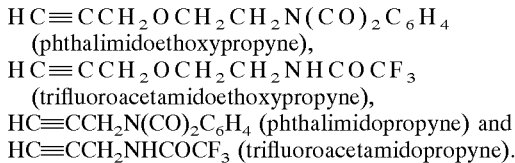

In these examples, the nucleosides which are obtained in this scheme are incorporated into the desired ODN, and the alkylating portion of the cross-linking agent is attached to the terminal amino group only after removal of the respective phthalic or trifluoroacetyl blocking groups.

Another particularly preferred example of an "arm-leaving group combination" (A-L) is attachment of a nitrogen-mustard type alkylating agent (or other alkylating agent) to the amino function of a 5-(3-aminopropyl)-2'-deoxyuridine building unit of the ODN. The appropriate nucleotide building unit for ODN synthesis which includes the 5-(3-aminopropyl)-2'-deoxyuridine nucleoside moiety can be obtained in analogy to Reaction Scheme 1, and in accordance with the teaching of Meyer et al. (1989) *J. Am. Chem. Soc.* 111:8517–8519. In this particularly preferred embodiment the nucleotide having the 5-(3-aminopropyl)-2'-deoxyuridine moiety is incorporated into the ODN by routine synthesis, and the cross-linking function is introduced by reacting the ODN with an activated form of a "nitrogen mustard", such as 2,3,5,6-tetrafluorophenyl-4'-[bis(2-chloroethyl)amino]phenylbutyrate (Chlorambucil 2,3,5,6-tetrafluorophenyl ester; chlorambucil itself is commercially available).

Other examples of nucleotides where the crosslinking agent is attached to a heterocyclic base are 2'-deoxy-4-aminopyrazolo[3,4-d]pyrimidine derivatives. The general structure of these derivatives is disclosed in co-owned PCT publication WO 90/03370. These compounds can be made from 3,4-disubstituted and 3,4,6-trisubstituted pyrazolo[3,4-d]pyrimidines, in accordance with the teaching of Kobayashi (1973) *Chem. Pharm. Bull.* 21:941–951. In these compounds, the arm A is attached at the 3-position, which is equivalent to the 7-position of the purines.

Discussing still in general terms the structures of the modified ODNs of the present invention, it is noted that examination of double-stranded DNA by ball-and-stick models and high resolution computer graphics indicates that the 7-position of the purines and the 5-position of the pyrimidines lie in the major groove of the B-form duplex of double-stranded nucleic acids. These positions can be substituted with side chains of considerable bulk without interfering with the hybridization properties of the bases. Additional sites for substitution according to the invention include C8 of purines, $N^2$ of guanine, and C3 of pyrazolopyrimidines. These side arms can be introduced either by derivatization of deoxythymidine, deoxyuridine, deoxycytidine, deoxyguanosine or deoxyadenosine (or analogues of these naturally-occurring bases), or by straightforward total synthesis of the heterocyclic base, followed by glycosylation. These modified nucleosides can be converted into the appropriate activated nucleotides for incorporation into oligonucleotides with an automated DNA synthesizer. With the pyrazolo[3,4-d]pyrimidines, which are analogs of adenine, the electrophilic arm is attached at the 3-position, which is equivalent to the 7-position of purine.

The arm A should be of sufficient length to reach across the major groove from a purine 7- or 8-position, pyrimidine 5-position, pyrrolopyrimidine 5-position or pyrazolopyrimidine 3-position and react with the N-7 of a purine (preferably guanine) in or adjacent to the target DNA sequence. The arm A holds the electrophilic group-leaving group combination E-L away from the base (to which it is covalently attached) when that base is paired with another within a double-stranded or triple-stranded complex. As noted above, broadly the arm A should have a length equivalent to 2–80 atoms, preferably 2–40 atoms. In general, the arms include alkylene groups of 1 to 12 carbon atoms, alkenylene groups of 2 to 12 carbon atoms and 1 or 2 olefinic bonds, alkynylene groups of 2 to 12 carbon atoms and 1 or 2 acetylenic bonds, or such groups substituted at a terminal point with nucleophilic groups (L) such as oxy, thio, amino or chemically blocked derivatives thereof (e.g., trifluoroacetamido, phthalimido, CONR', NR'CO, and SO$_2$NR', where R'=H or $C_{1-6}$ alkyl). Such functionalities, including aliphatic or aromatic amines, exhibit nucleophilic properties and are capable of serving as a point of attachment to such groups as:

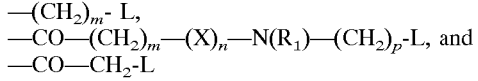

which are described above as components of exemplary cross-linking functional groups.

After the nucleoside or nucleotide unit which carries the crosslinking functionality A-L, or a suitable precursor thereof, (such as the —(CH$_2$)$_q$—NH$_2$ or —(CH$_2$)$_q$—Y group, where Y terminates with a nucleophilic group such as NH$_2$) is prepared, further preparation of the modified oligonucleotides of the present invention can proceed in accordance with state-of-the-art. Thus, to prepare oligonucleotides, protective groups are introduced onto the nucleosides or nucleotides and the compounds are activated for use in the synthesis of oligonucleotides. The conversion to protected, activated forms follows the procedures as described for 2'-deoxynucleosides in detail in several reviews. See Sonveaux (1986) *Bioorganic Chemistry* 14:274–325; and Jones (1984) in "Oligonucleotide Synthesis: A Practical Approach", M. J. Gait, ed., IRL Press, pp. 23–34.

The activated nucleotides are incorporated into oligonucleotides in a manner analogous to that for DNA and RNA nucleotides, in that the activated nucleotides will be sequentially linked to form a chain of nucleotides which is complementary to a sequence of nucleotides in target DNA. The nucleotides can be incorporated either enzymatically or via chemical synthesis. The nucleotides can be converted to their 5'-O-dimethoxytrityl-3'-(N,N-diisopropyl)phosphoramidite cyanoethyl ester derivatives, and incorporated into synthetic oligonucleotides following the procedures in "Oligonucleotide Synthesis: A Practical Approach", supra. The N-protecting groups are then removed, along with the other oligonucleotide blocking groups, by post-synthesis aminolysis, by procedures generally known in the art.

In a preferred embodiment, the activated nucleotides are used directly on an automated DNA synthesizer according to the procedures and instructions of the particular synthesizer employed. The oligonucleotides can be prepared on the synthesizer using the standard commercial phosphoramidite or H-phosphonate chemistries. The modified oligonucleotides of the invention can, in addition, comprise optional intercalators, lipophilic groups, minor groove binders, reporter groups, chelating agents or chemical "tails."

A moiety containing the electrophilic group-leaving group combination E-L, such as a haloacyl group (CO—CH$_2$-L where L is halogen for example I) or —CO—(CH$_2$)$_m$—(X)$_n$—N(R$_1$)—(CH$_2$)$_p$-L (even more preferably CO—(CH$_2$)$_3$—C$_6$H$_4$—N—[CH$_2$CH$_2$Cl]$_2$) can be added to the aminoalkyl or like groups [—(CH$_2$)$_q$—Y] following incorporation into oligonucleotides and removal of any blocking groups. For example, addition of an α-haloacetamide can be verified by a changed mobility of the modified compound on HPLC, corresponding to the removal of the positive charge of the amino group, and by subsequent readdition of a positive charge by reaction with 2-aminoethanethiol to give a derivative with reverse phase HPLC mobility similar to the original aminoalkyl-oligonucleotide.

In the situations where the cross linking agent (A-L moiety) is attached to the 3' or 5' terminus of the oligonucleotide, for example by an alkylamine linkage of the formula —(CH$_2$)$_q$—Y (Y terminating in an amine), the oligonucleotide synthesis can be performed to first yield the oligonucleotide with said aminoalkyl tail, to which then an alkylating moiety, such as the above-noted haloacyl group (CO—CH$_2$-L) or —CO—(CH$_2$)$_m$—(X)$_n$—N(R$_1$)—(CH$_2$)$_p$-L is introduced.

Another type of crosslinking agent that can be attached to oligonucleotides and is useful in the method of the present invention is the cyclopropapyrroloindole moiety, as disclosed by Lukhtanov et al. (1996) *Nucleic Acids Res.* 24:683–687, the disclosure of which is hereby incorporated by reference in its entirety.

According to the present invention, one or more electrophilic groups can be covalently attached to an oligonucleotide. A single electrophilic group can be attached at the 5' terminus, the 3' terminus, or at an internal nucleotide residue. If two crosslinking agents are present, they can be attached such that one is at each of the 5'- and 3'-ends of the ODN, or one can be attached at either the 5' or 3' end and the other attached at an internal nucleotide residue, both can be attached to internal nucleotide residues, or a bifunctional crosslinking agent can be attached at the 5' end, the 3' end or at an internal nucleotide residue.

Additional disclosure related to triple-strand-forming ODNs and crosslinking agents can be found in the following co-owned PCT Publications: WO 90/03370, WO 90/14353, WO 93/03736, WO 94/17092, and WO 96/40711, the disclosures of which are hereby incorporated by reference in their entirety.

Other Aspects of the Method

The methods described in the present application can be performed in vitro, for example to modify isolated, purified DNA or to modify the genome of a cultured cell. The methods can also be practiced ex vivo. Ex vivo describes the process wherein cells are removed from the body of a subject, cultured briefly and subjected to a therapeutic treatment (such as can be achieved by the practice of the present invention) prior to their return to the body of the subject. The ex vivo procedure is especially applicable to various hematologic and myeloid disorders including, but not limited to leukemia, lymphoma and various immune dysfunctions. Finally, the methods of the invention can be practiced in vivo, by administration of a modified oligonucleotide of the invention to a living subject.

The modified ODNs of the invention are administered to cells by any method of nucleic acid transfer known in the art, including, but not limited to, transformation, co-precipitation, electroporation, neutral or cationic liposome-mediated transfer, microinjection or gene gun. The modified ODNs can be attached to carriers and/or connected to carriers by cleavable linkers, such carriers and linkers including, but not limited to, those disclosed in co-owned U.S. Pat. No. 5,574,142. The modified ODNs of the invention are suitable for in vitro, in vivo and ex vivo therapy and can be administered parenterally, intravenously, subcutaneously, orally or by any other method known in the art. The modified ODNs of the invention can be combined with a pharmaceutically acceptable excipient for administration to a mammalian subject. The formulation of such pharmaceutically acceptable excipients is well within the skill of one in the art. A pharmaceutically acceptable excipient is preferably nontoxic and nontherapeutic. Examples of such excipients are water, saline, phosphate-buffered saline, Ringer's solution, dextrose solution, and Hank's solution. Nonaqueous vehicles, such as fixed oils, sesame oil, ethyl oleate, or triglycerides can also be used. Parenteral vehicles can also take the form of suspensions containing viscosity-enhancing agents, such as carboxymethylcellulose, sorbitol or dextran. The excipient will also usually contain minor amounts of substances that enhance isotonicity and chemical stability. Examples of buffers include, but are not limited to phosphate buffer, bicarbonate buffer and Tris buffer; while examples of preservatives include, but are not limited to thimerosal, m- or o-cresol, formalin and benzyl alcohol. Standard formulations will be either liquids or solids which can be dissolved in a suitable liquid medium as a suspension or a solution. Thus, in a non-liquid formulation, the vehicle can comprise dextrose, human serum albumin, preservatives, etc., to which sterile water, saline, buffer or other solvent can be added prior to administration.

The target sequence can reside in a chromosomal gene of a subject plant or animal, or in the genome of a virus, bacteria, fungus or other pathogen which can be present in the cells of a subject.

The modified oligonucleotides of the invention can interact with their target sequences in one of several fashions. For example, a modified oligonucleotide can interact with its target through triplex formation. Triplex formation can proceed through Hoogsteen- or reverse Hoogsteen-type base-pairing, in which two H-bonds are formed between a base in the modified oligonucleotide and a base in the target that is already base-paired, in the Watson-Crick sense, as part of a duplex nucleic acid. Equivalent types of triple-strand base-pairing are also contemplated by the present invention.

A triplex stabilizer can be used to facilitate triplex formation between the modified oligonucleotides of the invention and the target sequence. Triplex stabilizers intercalate preferentially into triplex, as opposed to duplex, nucleic acids and, through enhanced stacking interactions, facilitate the binding of the third strand to the Watson/Crick-paired duplex. A preferred triplex stabilizer is coralyne. Lee et al. (1993) *Biochemistry* 32:5591–5597. Other triplex stabilizers include benzo[α]pyridoquinoxalines (Marchand et al. (1996) *Biochemistry* 35:5022–5032), naphthylquinolines (Wilson et al. (1993) *Biochemistry* 32:10614–10621), and related molecules.

It is also possible for the modified oligonucleotide of the invention to interact with its target sequence in a process mediated by a recombinase enzyme. The use of a recombinase enzyme in concert with a triplex-forming anti-gene oligonucleotide significantly enhances the ability of the modified oligonucleotide to seek out and bind to its target sequence. According to another aspect of the invention, the modified oligonucleotide has at least about 26 nucleotides in a continuous sequence which are substantially homologous, in the Watson-Crick sense, to the target DNA. In the presence of a recombinase enzyme, such modified oligonucleotides are able to interact with the target sequence according to the rules of Watson-Crick base-pairing.

Sequence specific binding of the ODN to a double stranded DNA or DNA fragment and cross-linking to one DNA strand occurs in accordance with this aspect of the invention based on a "4-letter" Watson-Crick type recognition motif. It has been found however that in vitro a recombinase enzyme is needed for the binding and cross-linking to occur. The recombinase enzyme promotes binding of the ODN to the double-stranded DNA as a triplex. In vivo, recombinase enzymes are virtually ubiquitous and the ODNs in accordance with this aspect of the invention undergo triplex formation and resultant cross-linking due to the presence of the endogenous recombinase enzyme in the cell. The invention however is not limited by the specific nature or origin of the recombinase enzyme, recombinases from single cell organisms as well as from cells of human or mammalian origin are capable of functioning within the invention. Furthermore, modified recombinase enzymes are also useful in the method of the invention. For instance, Kido et al. (1992) *Exp. Cell Res.* 198:107–114 have disclosed a modified recA containing a nuclear localization signal; such modified recombinases and their equivalents are also useful in the practice of this embodiment of the invention.

Because binding and cross-linking of the ODN to double stranded DNA occurs on the basis of the full "4-letter" Watson Crick recognition motif, this aspect of the invention provides a still broader basis for therapeutic application and as a sequence specific probe (for example for gene mapping) of double stranded DNA than the previously described aspect of the invention wherein the binding of the ODN to the double-stranded DNA is based on Hoogsteen or reverse Hoogsteen (or equivalent) pairing.

Since the action of a recombinase enzyme is necessary in accordance with this aspect of the invention, the ODNs designed in accordance with this aspect include sugar moieties in their nucleotide units which are compatible with recognition by the recombinase enzyme. Preferably the ODNs in accordance with this aspect comprise 2'-deoxyribonucleotides and their isosteric equivalents, 2'-O-alkyl ribonucleotides (alkyl of $C_1$–$C_6$ carbons) and 2'-deoxy-2-fluororibonucleotides.

It is an important feature or discovery in accordance with this aspect of the invention that the entire ODN does not need to be homologous (or complementary) to the double-stranded DNA or fragment thereof, but there should preferably be at least approximately 26, and more preferably at least approximately 30 nucleotide units in a continuous sequence in the ODN which are homologous (or substantially homologous) to the matching sequence of the double-stranded DNA (or fragment thereof). Moreover, the cross-linking function should preferably be within or attached to an end of the continuous sequence of approximately 26, or more, homologous (or substantially homologous) nucleotide units.

Advantages of the Method

Binding of a modified oligonucleotide of the invention to its target sequence places the attached electrophilic group in proximity to a functional group on an adjacent or nearby nucleotide. Such functional groups include, but are not limited to, the N3 and N7 atoms of guanine and adenine, the N1 atom of adenine, the N3 atom of cytosine and the O6 atom of guanine. When so positioned, the electrophilic group has a high probability of reacting with the functional group, thereby generating a potentially mutagenic lesion. In vivo, when the DNA comprising the potentially mutagenic lesion is subjected to cellular replication and/or repair processes, the lesion can become converted into a mutation. Mutation can occur in one of several ways: by a change in nucleotide sequence, by insertion, by deletion or by transposition.

Certain mutations can result in a change of function of the mutated gene. Some examples of mutations which alter gene function include, but are not limited to, insertion or deletion of one or more nucleotides leading to a change in the reading frame of the encoded protein, conversion of a coding sequence to a translational stop codon, a change in a mRNA splicing signal, changes in promoter or enhancer sequences affecting transcriptional initiation, changes to 5' untranslated sequences that reduce or abolish translational initiation, sequence changes within the coding region that reduce the rate of transcriptional elongation, and alterations in the 3' untranslated region leading to altered mRNA stability. It should be appreciated that, in certain cases, the method of the invention is also useful in correcting a defect in a gene, thereby restoring its activity or altering its activity to resemble more closely that of the corresponding normal gene.

In order to achieve targeted modification at a specific sequence in a living cell, it is desirable to ensure that the majority of modified oligonucleotides that bind to a target sequence become covalently attached to that sequence. Since hybridization is a reversible process, it is necessary for reaction of the electrophilic group of the modified oligonucleotide to occur shortly after hybridization, and not be dependent on outside activation. Since the modified oligonucleotides of the present invention are inherently capable of forming crosslinks with their target sequences, exogenous activation of the reactive group is not required, as is the case with photoactivatible crosslinking agents. Hence, the method of the present invention does not require light or any other outside agent to facilitate crosslinking. Since crosslinking by the modified ODNs of the invention does not require external activation subsequent to formation of a triple-stranded complex between the mutagenic oligonucleotide of the invention and its target sequence, the majority of binding events will generate a crosslink. Consequently, the mutagenic efficiency of the method of the present invention is much higher than that of previous methods, in which only that fraction of the modified oligonucleotides that were bound to the target at the time the external activating stimulus was applied were capable of even potentially generating a mutation.

The following examples are provided to illustrate but not limit the invention.

EXAMPLES

The shuttle vector plasmid used in these experiments was pSP189. Parris et al. (1992) *Gene* 117:1–5. It contains an *Escherichia coli* supF tRNA gene, a mammalian DNA replication origin, a procaryotic DNA replication origin and an ampicillin resistance marker. The supF tRNA gene was used as a target for mutagenesis in these experiments. This gene is contained on a 160-nucleotide restriction fragment bordered by EcoRI and MluI restriction sites. The nucleotide sequence of the region of this fragment encompassing the supF tRNA gene is shown in FIG. 1 (SEQ ID NO: 1 and 2). The following experiment demonstrates that the modified oligonucleotides of the invention are crosslinking within the target sequence of the plasmid and that the crosslinking is causing specific changes in the nucleotide sequence of pSP189.

Treatment of Plasmid DNA with Modified Oligonucleotide

In these experiments, $10^{-7}$ M modified oligonucleotide was used for mutagenesis of $10^{-8}$ M supercoiled pSP189 DNA, to give a 10-fold molar excess of modified oligonucleotide to target. Sequences of the modified oligonucleotides used in these experiments are given in FIG. 1 and are shown below.

```
ODN1 (Rec069.08) 5' CTCGAGCTGTGGUGGGGTUCCCGAGCGGCC 3'     SEQ ID NO:3

ODN2 (Rec069.09) 5' CTCGAGCTGTGGUGGGGTTCCCGAGCGGCC 3'     SEQ ID NO:4

ODN3 (Rec069.07) 5' CTCGAGCTGTGGTGGGGTUCCCGAGCGGCC 3'     SEQ ID NO:5

ODN4 (Rec569.03) 5' GGCCGCTCGGGAACCCCACCACAGCTCGAG 3'     SEQ ID NO:6

ODN5 (Rec569.04) 5' GGCCGCTCGGGAACCCCACCACAGCTCGAG 3'     SEQ ID NO:7

ODN6 5'TCTGCCGTCATCGACTTCGAAGGTTCGAATCCT                  SEQ ID NO:8
UCCCCCACCACCACGGC

ODN7 5'TCTGCCGUCATCGACTTCGAAGGTTCGAATCCT                  SEQ ID NO:9
UCCCCCACCACCACGGC
```

ODNs 1, 2, 3, 6, and 7 are shown in FIG. 1, aligned with the sequence of the supF gene. U represents chlorambucil conjugated through 5-(3-aminopropyl)-2'-deoxyuridine. A represents chlorambucil conjugated through 3-(3-aminopropyl)-4-amino-1-(2'-deoxy-β-D-ribofuranosyl)-pyrazolo[3,4-d]pyrimidine. The sequence of ODNs 4 and 5 is complementary to that of ODNs 1, 2 and 3. Results from all seven of these modified oligonucleotides are summarized in Table 1. Sequence changes shown in FIG. 2 are the result of treatment with ODNs 1, 2 and 3.

Nucleic acids were combined in a final volume of 50–100 μl along with the following reagents: $2.5 \times 10^{-6}$ M E. coli recA (New England Biolabs, Inc.); 10 mM Tris-base (pH 7.4 with acetic acid); 50 mM sodium acetate; 1 mM dithiothreitol; 1 mM γ-S-ATP (Boehringer-Mannheim); 5% (v/v) glycerol and 12 mM magnesium acetate. The mixture was incubated at 37° C. for 6 hours. Following incubation, sodium dodecylsulfate was added to 0.5% (w/v) and proteinase K (Sigma) was added to 200 μg/ml and the mixture was incubated for one hour at 37° C. The mixture was then extracted with phenol-chloroform-isoamyl alcohol (25:24:1 v/v/v) followed by ether extraction. The modified plasmid DNA was then precipitated with 2½–3 volumes of ethanol. A sample of DNA was analyzed for DNA crosslinking.

Quantification of Crosslinking Between Oligonucleotide and Plasmid

The samples were divided into two equal portions. One portion was resuspend in 50 μl EcoRI buffer (New England Biolabs), and 20 units EcoRI was added; the solution was incubated at 37° C. for 1 hr. The second portion was resuspended in 50 μl MluI buffer (New England Biolabs), then 10 units MluI was added and the solution was incubated at 37° C. for 1 hr. To the samples was then added 100 μl BAP buffer (US Biochemicals), followed by 0.6 Units (1 μl) BAP (bacterial alkaline phosphatase, US Biochemicals). This solution was incubated for 1 hour at 37° C. The mixture was then extracted with phenol-chloroform-isoamyl alcohol (25:24:1 v/v/v) followed by ether extraction. The modified DNA restriction fragments were then precipitated with 2½–3 volumes of ethanol, washed with 70% ethanol, and dried in vacuo.

The free 5'-ends of the fragments were labeled by resuspending in 50 μl kinase buffer and addition of 2 μl [γ-$^{32}$P] ATP and 1 μl T4 polynucleotide kinase (New England Biolabs); the solution was incubated for 1 hour at 37° C. The mixture was then extracted with phenol-chloroform-isoamyl alcohol (25:24:1, v/v/v) followed by ether extraction. The modified DNA restriction fragments were then precipitated with 2½–3 volumes of ethanol, washed with 70% ethanol, and dried in vacuo.

Each of the two portions from each reaction was then resuspended in 50 μl restriction buffer and digested with the OPPOSITE restriction enzymes (MluI to treat the previously EcoRI digested samples and vice versa). The mixture was then extracted with phenol-chloroform-isoamyl alcohol (25:24:1 v/v/v) followed by ether extraction. The modified DNA restriction fragments were then precipitated with 2½–3 volumes of ethanol, washed with 70% ethanol, and dried in vacuo.

The samples were resuspended in 10 μl loading dye, and 1–2 μl of each sample was run on a 4% denaturing polyacrylamide gel. Care was taken to assure that the gels were not allowed to heat over room temperature. The percent mono- and bis-crosslinking were determined by phosphorimaging and calculating the ratio of the unreacted 160-base restriction fragment to those bands migrating more slowly in the gel. The monocrosslinked bands (of which there may be several) had a mobility in the expected range for the 160+30 (or 50) nucleotides of the reactive ODN, and the bis-crosslinked fragments had mobilities expected for 2×160+30 (or 50) nucleotides. The data are summarized in Table 1.

Transfection of Plasmid into COS-7 Cells

COS-7 cells were obtained from the American Type Culture Collection and maintained with Dulbecco's modified Eagle's medium (DMEM) supplemented with 10% fetal calf serum. Prior to transfection, cells were plated at a density of $1 \times 10^4$ cells/cm$^2$.

Modified plasmid DNA was mixed with DOTAP (Boehringer-Mannheim) at a ratio of 5 μg DOTAP to 1 μg plasmid DNA as recommended by the manufacturer. The DOTAP/plasmid mixture was added to $2 \times 10^5$ cells at a concentration of 2.5 μg plasmid in a final volume of 2.0 mls of DMEM. Cells were incubated at 37° C. for 12–16 hours in a 5% CO$_2$ environment The DOTAP/plasmid containing medium was then replaced with fresh DMEM containing 10% fetal calf serum and incubated an additional 48 hours. After incubation, the plasmid DNA was purified and treated with endonuclease DpnI (Gibco) as described by Seidman, et al. Gene (1985) 38:233–237.

Mutation analysis of the supF gene was carried out following transformation of an indicator strain of Escherichia coli (MBM7070) by electroporation. Transformed cells were grown as described by Havre et al. (1993) J. Virology 67:7324–7331. The results, expressed as per cent mutations, are summarized in Table 1.

TABLE 1

Results of crosslinking reactive ODNs to pSP189 shuttle vector plasmid, and mutagenesis of the crosslinked plasmid in cells.

| Crosslinking Oligo-nucleotide ID | Number of white colonies[a] | Number of blue colonies[a] | % mutations[b] | % Bis-crosslinking[c] | % Mono-crosslinkin[d] |
|---|---|---|---|---|---|
| ODN2 | 11  | 2597 | 0.42 | 0.4 | 16.4 |
| "    | 9   | 1770 | 0.51 | 0.1 | 30.9 |
| ODN3 | 14  | 1349 | 1.04 | 5.7 | 33.6 |
| "    | 9   | 3282 | 0.27 | 0.3 | 37.8 |
| ODN1 | 120 | 5884 | 2.04 | 8.4 | 33.0 |
| "    | 10  | 582  | 1.72 | 7.8 | 55.9 |
| "    | 18  | 1422 | 1.27 | 7.3 | 30.8 |
| ODN4 | 18  | 1531 | 1.18 | 2.1 | 31.4 |
| ODN5 | 8   | 1926 | 0.42 | 2.7 | 55.9 |
| ODN6 | 51  | 4500 | 1.13 | 2.2 | 38.7 |
| ODN7 | 102 | 6500 | 1.57 | 4.6 | 18.0 |

[a]White or blue colonies of bacteria transformed by the supF gene in the pSP 189 plasmid assay.
[b]Ratio of white to blue colonies.
[c]Percentage of plasmid with both strands covalently bound by the test oligonucleotide
[d]Percentage of plasmid with one strand covalently bound by test oligonucleotide, expressed as the sum of monocrosslinking to either strand.

Plasmid DNA was isolated for sequencing from overnight cultures using the Quantum Miniprep Kit (BioRad) as recommended by the manufacturer. DNA sequence data were obtained by direct chain termination sequencing of plasmid DNA by standard methods. Changes in nucleotide sequence of the supF gene induced by treatment with the modified oligonucleotides of the invention are shown in FIG. 2.

The data clearly show that the covalent attachment of the reactive ODN to the supF gene of this shuttle vector is highly mutagenic. When the frequency of mutations is correlated with the percentage of both mono- and bis-crosslinkage using multiple regression analysis, the following equation is obtained:

$$MF = 0.18 \ (+/-0.04) \ BIS + 0.008 \ (+/-0.005) \ MONO$$

where

MF=percentage mutation frequency

BIS=percentage biscrosslinked plasmid (averaged for amount of biscrosslink found on both restriction fragments)

MONO=percentage monocrosslinked plasmid (sum of monocrosslink to each fragment)

This indicates that plasmids which undergo biscrosslinking, have a mutation rate of about 18%, a remarkably high value. Furthermore, almost all the mutations were at or immediately adjacent to the targeted site (see FIG. 2). These data support the surprising findings that a) oligonucleotides bound to a target site by a covalent bond induce higher rates of mutagenesis than simpler modifications, and b) the biscrosslinked species has a remarkable and unprecedentedly high rate of site directed mutation of the target.

Examples of in vitro site-specific modification of target DNA sequences using modified oligonucleotides are provided in co-owned PCT Publication WO 96/40711, the disclosure of which is hereby incorporated by reference.

Although the foregoing invention has been described in some detail by way of illustration and example for purposes of clarity of understanding, it will be apparent to those skilled in the art that certain changes and modifications can be practiced. Therefore the foregoing descriptions and examples should not be construed as limiting the scope of the invention, which is delineated by the appended claims.

What is claimed is:

1. A modified oligonucleotide for site-directed mutagenesis of a double-stranded nucleic acid molecule comprising one or more mutagens incorporated into a single-stranded oligonucleotide, said oligonucleotide having a sequence that forms a triple-stranded nucleic acid molecule with a target sequence in the double-stranded nucleic acid molecule.

2. The oligonucleotide according to claim 1 wherein the target sequence is in a chromosomal gene of a plant or animal, a viral genome, or the genome of a pathogen.

3. The oligonucleotide according to claim 1 wherein the mutagen is an electrophilic group.

4. The oligonucleotide according to claim 1 wherein the mutagen is an alkylating agent.

5. The oligonucleotide according to claim 1 wherein two or more mutagens are attached to the oligonucleotide.

6. The oligonucleotide according to claim 5 wherein two or more alkylating agents are attached to the oligonucleotide.

7. A method for site-directed mutagenesis of a nucleic acid molecule comprising the steps of:
   a) contacting a modified oligonucleotide to a target sequence of a double-stranded nucleic acid molecule, wherein the modified oligonucleotide comprises one or more mutagens incorporated into a single-stranded nucleic acid that forms a triple-stranded nucleic acid molecule with the target region; and
   b) thereby mutating the double-stranded nucleic acid molecule.

8. The method according to claim 7 wherein the target sequence is in a chromosomal gene of a plant or animal, a viral genome, or the genome of a pathogen.

9. The method according to claim 7 wherein the mutagen is an electrophilic group.

10. The method according to claim 7 wherein the mutagen is an alkylating agent.

11. The method according to claim 7 wherein two or more mutagens are attached to the oligonucleotide.

12. The method according to claim 7 wherein two or more alkylating agents are attached to the oligonucleotide.

13. The method according to claim 7 wherein the mutagenesis alters the activity of the double-stranded nucleic acid molecule.

14. A method of producing a mutagenic oligonucleotide comprising the steps of:
   a) synthesizing an oligonucleotide which forms a triple-stranded nucleic acid molecule with a target sequence of a double-stranded nucleic acid molecule; and
   b) covalently attaching one or more mutagens to the oligonucleotide.

15. The method according to claim 14 wherein the target sequence is in a chromosomal gene of a plant or animal, a viral genome, or the genome of a pathogen.

16. The method according to claim 14 wherein the mutagen is an electrophilic group.

17. The method according to claim 14 wherein the mutagen is an alkylating agent.

18. The method according to claim 14 wherein two or more mutagens are attached to the oligonucleotide.

19. The method according to claim 14 wherein two or more alkylating agents are attached to the oligonucleotide.

20. The method according to claim 14 wherein the mutagen is incorporated into the oligonucleotide during synthesis of the oligonucleotide.

21. The method according to claim 14 wherein the mutagen is incorporated into the oligonucleotide subsequent to synthesis of the oligonucleotide.

22. The method according to claim 7 wherein the oligonucleotide comprises at least about 26 nucleotides and wherein the oligonucleotide forms a triple-stranded complex with the target according to the rules of Watson/Crick base pairing,
   the method further comprising contacting the oligonucleotide with a recombinase.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
        (A) LENGTH: 124 base pairs
        (B) TYPE: nucleic acid
        (C) STRANDEDNESS: single
        (D) TOPOLOGY: linear (xi) SEQUENCE DESCRIPTION: SEQ ID NO:1:

CTGCTCGAGC TGTGGTGGGG TTCCCGAGCG GCCAAAGGGA GCAGACTCTA AATCTGCCGT    60

CATCGACTTC GAAGGTTCGA ATCCTTCCCC CACCACCACG GCCGAAATTC GGTACCCGGA   120

```
TCCT                                                                        124

(2) INFORMATION FOR SEQ ID NO:2:

(i) SEQUENCE CHARACTERISTICS:
        (A) LENGTH: 124 base pairs
        (B) TYPE: nucleic acid
        (C) STRANDEDNESS: single
        (D) TOPOLOGY: linear (xi) SEQUENCE DESCRIPTION: SEQ ID NO:2:

AGGATCCGGG TACCGAATTT CGGCCGTGGT GGTGGGGGAA GGATTCGAAC CTTCGAAGTC            60

GATGACGGCA GATTTAGAGT CTGCTCCCTT TGGCCGCTCG GGAACCCCAC CACAGCTCGA          120

GCAG                                                                        124

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: group(13, 19)
        (D) OTHER INFORMATION: /note= "N represents Chlorambucil
            conjugated through 5-(3-aminopropyl)-2'-deoxyuridine"

(xi) SEQUENCE DESCRIPTION: SEQ ID NO:3:

CTCGAGCTGT GGNGGGGTNC CCGAGCGGCC                                             30

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 13
        (D) OTHER INFORMATION: /note= "N represents Chlorambucil
            conjugated through 5-(3-aminopropyl)-2'-deoxyuridine"

(xi) SEQUENCE DESCRIPTION: SEQ ID NO:4:

CTCGAGCTGT GGNGGGGTTC CCGAGCGGCC                                             30

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 19
        (D) OTHER INFORMATION: /note= "N represents Chlorambucil
            conjugated through 5-(3-aminopropyl)-2'-deoxyuridine"

(xi) SEQUENCE DESCRIPTION: SEQ ID NO:5:

CTCGAGCTGT GGTGGGGTNC CCGAGCGGCC                                             30

(2) INFORMATION FOR SEQ ID NO:6:
```

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: group(13, 18)
        (D) OTHER INFORMATION: /note= "N represents Chlorambucil
            conjugated through 3-(3-aminopropyl)-4-amino-1-
            (2'-deoxy-beta-d-ribofuranosyl)-pyr
            azolo[3,4-D] pyrimidine"

(xi) SEQUENCE DESCRIPTION: SEQ ID NO:6:

GGCCGCTCGG GANCCCCNCC ACAGCTCGAG                                            30

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 13
        (D) OTHER INFORMATION: /note= "N represents Chlorambucil
            conjugated through 3-(3-aminopropyl)-4-amino-1-
            (2'-deoxy-beta-d-ribofuranosyl)-pyr
            azolo[3,4-D] pyrimidine"

(xi) SEQUENCE DESCRIPTION: SEQ ID NO:7:

GGCCGCTCGG GANCCCCACC ACAGCTCGAG                                            30

(2) INFORMATION FOR SEQ ID NO:8:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 34
        (D) OTHER INFORMATION: /note= "N represents Chlorambucil
            conjugated through 5-(3-aminopropyl) -2'-deoxyuridine"

(xi) SEQUENCE DESCRIPTION: SEQ ID NO:8:

TCTGCCGTCA TCGACTTCGA AGGTTCGAAT CCTNCCCCCA CCACCACGGC                      50

(2) INFORMATION FOR SEQ ID NO:9:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: group(8, 34)
        (D) OTHER INFORMATION: /note= "N represents Chlorambucil
            conjugated through 5-(3-aminopropyl)-2'-deoxyuridine"

(xi) SEQUENCE DESCRIPTION: SEQ ID NO:9:

TCTGCCGNCA TCGACTTCGA AGGTTCGAAT CCTNCCCCCA CCACCACGGC                      50